(12) United States Patent
Moeller et al.

(10) Patent No.: US 6,203,579 B1
(45) Date of Patent: Mar. 20, 2001

(54) USE OF 1-SUBSTITUTED ISATINS TO DYE FIBERS CONTAINING KERATIN

(75) Inventors: Hinrich Moeller, Monheim; Horst Hoeffkes, Duesseldorf; Bernd Meinigke, Leverkusen; David Rose, Hilden, all of (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 0 days.

(21) Appl. No.: 09/403,726

(22) PCT Filed: Apr. 15, 1998

(86) PCT No.: PCT/EP98/02199

§ 371 Date: Oct. 22, 1999

§ 102(e) Date: Oct. 22, 1999

(87) PCT Pub. No.: WO98/47472

PCT Pub. Date: Oct. 29, 1998

(30) Foreign Application Priority Data

Apr. 24, 1997 (DE) .............................. 197 17 282

(51) Int. Cl.[7] ........................................ A61K 7/13
(52) U.S. Cl. .................. 8/409; 8/405; 8/407; 8/410; 8/423; 8/574
(58) Field of Search .............. 8/405, 409, 410, 8/411, 412, 423, 574, 407

(56) References Cited

U.S. PATENT DOCUMENTS

| | | | |
|---|---|---|---|
| 4,921,503 | * 5/1990 | Anderson et al. | 8/408 |
| 4,931,218 | 6/1990 | Schenker et al. | 252/551 |
| 5,294,726 | 3/1994 | Behler et al. | 554/98 |
| 5,611,817 | * 3/1997 | Moeller et al. | 8/423 |
| 5,616,150 | 4/1997 | Moeller et al. | 8/405 |
| 5,743,919 | 4/1998 | Moeller et al. | 8/409 |

FOREIGN PATENT DOCUMENTS

| | | |
|---|---|---|
| 37 23 354 | 1/1989 | (DE) . |
| 39 26 344 | 2/1991 | (DE) . |
| 0 740 741 | 11/1996 | (EP) . |
| WO93/19725 | 10/1993 | (WO) . |
| WO94/08970 | 4/1994 | (WO) . |
| WO94/24988 | 11/1994 | (WO) . |
| WO94/24989 | 11/1994 | (WO) . |
| WO95/24886 | 9/1995 | (WO) . |

OTHER PUBLICATIONS

The Science of Hair Care, 7, pp. 248–250.
The Science of Hair Care, 8, pp. 264–267.

\* cited by examiner

*Primary Examiner*—Caroline D. Liott
(74) *Attorney, Agent, or Firm*—Wayne C. Jaeschke; Glenn E. J. Murphy; Kimberly R. Hild

(57) ABSTRACT

A colorant composition for coloring keratin-containing fibers is disclosed having (a) at least one isatin derivative corresponding to the formula I:

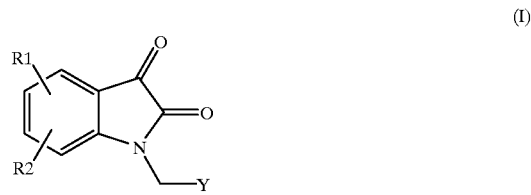

where $R^1$ and $R^2$ independently of one another represent a hydrogen atom, a halogen atom, a hydroxy group, a $(C_{1-4})$-alkyl, hydroxy-$(C_{1-4})$-alkyl, tertiary amino-$(C_{1-4})$-alkyl, $(C_{1-4})$-alkoxy group, an amino group optionally substituted by one or two $(C_{1-4})$-alkyl or hydroxy-$(C_{1-4})$-alkyl groups, a nitro, carboxy, or sulfo group, and Y is a hydroxy group, a $(C_{1-4})$-alkoxy group or an amino group which may be substituted by $(C_{1-4})$-alkyl, $(C_{1-4})$-alkoxy-$(C_{1-4})$-alkyl, carboxy-$(C_{1-4})$-alkyl, sulfo-$(C_{1-4})$-alkyl or hydroxy-$(C_{1-4})$-alkyl groups or which may be part of a heterocyclic 5-, 6- or 7-membered ring, or physiologically compatible salts thereof, and (b) at least one compound containing a primary or secondary amino group or hydroxy group selected from the group consisting of primary or secondary aliphatic or aromatic amines, nitrogen-containing heterocyclic compounds, amino acids, oligopeptides made up of 2 to 9 amino acids, aromatic hydroxy compounds, and CH-active compounds. The coloring composition does not require oxidizing agents and has very little, if any, sensitizing potential.

16 Claims, No Drawings

USE OF 1-SUBSTITUTED ISATINS TO DYE FIBERS CONTAINING KERATIN

This application is filed under 35 U.S.C. 371 and based on PCT/EP98/02199, filed Apr. 15, 1998.

BACKGROUND OF THE INVENTION

1. Field of the Invention

This invention relates to the use of 1-substituted isatins for coloring keratin-containing fibers, more especially human hair.

2. Discussion of Related Art

In general, keratin-containing fibers, for example hair, wool or pelts, are dyed either with substantive dyes or with oxidation dyes which are formed by oxidative coupling of one or more primary intermediates with one another or with one or more secondary intermediates. Primary and secondary intermediates are also known as oxidation dye precursors.

The primary intermediates normally used are primary aromatic amines containing another free or substituted or amino group in the para or ortho position, diaminopyridine derivatives, heterocyclic hydrazones, 4-aminopyrazolone derivatives and 2,4,5,6-tetraaminopyrimidine and derivatives thereof.

Special representatives are, for example, p-phenylenediamine, p-toluylenediamine, p-aminophenol, o-aminophenol, 1-(2'-hydroxyethyl)-2,5-diaminobenzene, N,N-bis-(2-hydroxyethyl)-p-phenylenediamine, 2-(2,5-diaminophenoxy)-ethanol, 1-phenyl-3-carboxyamido-4-amino-5-pyrazolone, 4-amino-3-methylphenol, 2,4,5,6-tetraaminopyrimidine, 2-hydroxy-4,5,6-triaminopyrimidine, 4-hydroxy-2,5,6-triaminopyrimidine, 2,4-dihydroxy-5,6-diaminopyrimidine, 2-dimethylamino-4,5,6-triaminopyrimidine, 2-hydroxyethylaminomethyl-4-aminophenol, 4,4'-diaminodiphenylamine, 4-amino-3-fluorophenol, 2-aminomethyl-4-aminophenol, 2-hydroxymethyl-4-aminophenol, bis-(2-hydroxy-5-aminophenyl)-methane, 1,4-bis-(4-aminophenyl) diazacycloheptane, 1,3-bis-(N-(2-hydroxyethyl)-N-(4-aminophenylamino))-2-propanol, 4-amino-2-(2-hydroxyethoxy)-phenol and 4,5-diaminopyrazole derivatives according to EP 0 740 741 or WO 94/08970, for example 4,5-diamino-1-(2'-hydroxyethyl)-pyrazole.

The secondary intermediates used are generally m-phenylenediamine derivatives, naphthols, resorcinol and resorcinol derivatives, pyrazolones and m-aminophenols. Particularly suitable secondary intermediates are 1-naphthol, pyrogallol, 1,5-, 2,7- and 1,7-dihydroxynaphthalene, o-aminophenol, 5-amino-2-methylphenol, m-aminophenol, resorcinol, resorcinol monomethyl ether, m-phenylenediamine, 1-phenyl-3-methyl-5-pyrazolone, 2,4-dichloro-3-aminophenol, 1,3-bis-(2,4-diaminophenoxy)propane, 4-chlororesorcinol, 2-chloro-6-methyl-3-aminophenol, 2-methyl resorcinol, 5-methyl resorcinol, 2,5-dimethyl resorcinol, 2,6-dihydroxypyridine, 2,6-diaminopyridine, 2-amino-3-hydroxypyridine, 2,6-dihydroxy-3,4-diaminopyridine, 3-amino-2-methylamino-6-methoxypyridine, 4-amino-2-hydroxytoluene, 2,6-bis-(2-hydroxyethylamino)-toluene, 2,4-diaminophenoxyethanol, 1-methoxy-2-amino-4-(2-hydroxyethylamino)-benzene, 2-methyl-4-chloro-5-aminophenol, 6-methyl-1,2,3,4-tetrahydroquinoxaline, 3,4-methylenedioxyphenol, 3,4-methylenedioxyaniline, 2,6-dimethyl-3-aminophenol, 3-amino-6-methoxy-2-methylaminophenol, 2-hydroxy-4-aminophenoxyethanol, 2-methyl-5-(2-hydroxyethylamino)-phenol and 2,6-dihydroxy-3,4-dimethyl pyridine.

With regard to the dyes suitable for use in the hair coloring and tinting formulations according to the invention, reference is also specifically made to Ch. Zviak's work *The Science of Hair Care*, Chapter 7 (pages 248–250; Substantive Dyes) and Chapter 8, pages 264–267; Oxidation Dye Precursors), published as Vol. 7 of the Series "*Dermatology*" (Editors: Ch. Culnan and H. Maibach), Marcel Dekker Inc., New York/Basel, 1986 and to the "*Europäische Inventar der Kosmetik-Rohstoffe*" published by the Europäische Gemeinschaft and available in diskette form from the Bundesverband Deutscher Industrie- und Handelsunternehmen für Arzneimittel, Reformwaren und Körperpflegemittel e.V., Mannheim, Germany.

Although intensive colors with good fastness properties can be obtained with oxidation dyes, the color is generally developed under the influence of oxidizing agents, such as $H_2O_2$ for example, which in some cases can result in damage to the fibers. In addition, some oxidation dye precursors or certain mixtures of oxidation dye precursors can occasionally have a sensitizing effect in people with sensitive skin. Although substantive dyes are applied under more moderate conditions, their disadvantage is that, in many cases, the colors obtained have inadequate fastness properties.

International patent applications WO 93/19725, WO 94/24988, WO 94/24989 and WO 95/24886 describe formulations for coloring keratin-containing fibers which contain isatin derivatives as their dye component.

The problem addressed by the present invention was to provide colorants for keratin fibers, more especially human hair, which would be at least equivalent in quality to conventional oxidation hair dyes in regard to depth of color, grey coverage and fastness properties, but which would not necessarily have to contain oxidizing agents, such as $H_2O_2$ for example. In addition, the colorants according to the invention would have very little, if any, sensitizing potential.

DESCRIPTION OF THE INVENTION

It has now surprisingly been found that certain isatin derivatives are eminently suitable for coloring keratin-containing fibers, even in the absence of oxidizing agents. They give colors with excellent brilliance and depth of color and lead to a wide variety of shades. In principle, however, oxidizing agents may still be present.

The present invention relates to the use of 1-substituted isatins corresponding to formula (I):

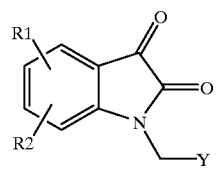

(I)

in which $R^1$ and $R^2$ independently of one another represent a hydrogen atom, a halogen atom, a hydroxy group, a $(C_{1-4})$-alkyl, hydroxy-$(C_{1-4})$-alkyl, tert.amino-$(C_{1-4})$-alkyl, $(C_{1-4})$-alkoxy group, an amino group optionally substituted by one or two $(C_{1-4})$-alkyl or hydroxy-$(C_{1-4})$-alkyl groups, a nitro, carboxy or sulfo group and Y is a hydroxy group, a $(C_{1-4})$-alkoxy group or an amino group which may be substituted by $(C_{1-4})$-alkyl, $(C_{1-4})$-alkoxy-$(C_{1-4})$-alkyl, carboxy-$(C_{1-4})$-alkyl, sulfo-$(C_{1-4})$-alkyl or hydroxy-$(C_{1-4})$-alkyl groups or which may be part of a heterocyclic 5-, 6- or 7-membered ring, or physiologically compatible salts thereof for coloring keratin-containing fibers, more especially human hair.

In the context of the invention, keratin-containing fibers are understood to include wool, pelts, feathers and, in particular, human hair. In principle, however, the colorants according to the invention may also be used to color other natural fibers such as, for example, cotton, jute, sisal, linen or silk, modified natural fibers such as, for example, regenerated cellulose, nitro, alkyl or hydroxyalkyl or acetal cellulose and synthetic fibers such as, for example, polyamide, polyacrylonitrile, polyurethane and polyester fibers.

The isatin derivatives corresponding to formula I are preferably selected from the group consisting of 1-hydroxymethyl isatin, 1-hydroxymethyl-5-methyl isatin, 1-hydroxymethyl-5-chloroisatin, 1-hydroxymethyl-5-sulfoisatin, 1-hydroxymethyl-5-carboxyisatin, 1-hydroxymethyl-5-nitroisatin, 1-hydroxymethyl-5-bromoisatin, 1-hydroxymethyl-5-methoxyisatin, 1-hydroxymethyl-5,7-dichloroisatin, 1-dimethylaminomethyl isatin, 1-diethylaminomethyl isatin, 1-(bis-(2-hydroxyethyl)-aminomethyl)-isatin, 1-(2-hydroxyethylaminomethyl)-isatin, 1-(bis-(2-hydroxypropyl)-aminomethyl)isatin, 1-pyrrolidinomethyl isatin, 1-piperidinomethyl isatin, 1-morpholinomethyl isatin, 1-(1,2,4-triazolyl)-methyl isatin, 1-(1-imidazolyl)-methyl isatin, 1-carboxymethylaminomethyl isatin, 1-(2-carboxyethylaminomethyl)-isatin, 1-(3-carboxypropylaminomethyl)-isatin, 1-(bis-(2-hydroxyethyl)-aminomethyl)-5-methyl isatin, 1-piperidinomethyl-5-chloroisatin, 1-(2-sulfoethylamino) isatin and the alkali metal and optionally ammonium salts of the acidic compounds, 1-hydroxymethyl isatin, 1-hydroxymethyl-5-methyl isatin, 1-hydroxymethyl-5-chloroisatin, 1-diethylaminomethyl isatin, 1-(bis-(2-hydroxyethyl)-aminomethyl)-isatin, 1-pyrrolidinomethyl isatin, 1-piperidinomethyl isatin, 1-morpholinomethyl isatin and 1-(3-carboxypropylaminomethyl)-isatin being particularly preferred.

The compounds corresponding to formula I are known from the literature or are commercially available.

Colorants containing isatin derivatives of formula I as their sole coloring component are preferably used for colors in the yellow range. Colors with even greater brilliance and further improved fastness properties, above all in the orange, brown, violet and black range, are obtained when the isatin derivatives corresponding to formula I are used together with compounds containing a primary or secondary amino group, for example aniline derivatives, with nitrogen-containing heterocyclic compounds, for example primary heteroaromatic amines, aromatic hydroxy compounds or CH-active compounds. These are, on the one hand, compounds which, on their own, have only a weak coloring effect on keratin-containing fibers and which only produce brilliant colors in conjunction with the isatins corresponding to formula I. However, they also include compounds which are known to be used as oxidation dye precursors.

The isatin derivatives corresponding to formula I are preferably used in a quantity of 0.03 to 65 mmol and more preferably in a quantity of 1 to 40 mmol, based on 100 g of the colorant as a whole. They may be used as substantive dyes or in the presence of oxidation dye precursors.

The present invention also relates to a preparation for coloring keratin-containing fibers, more especially human hair, which contains A at least one isatin derivative corresponding to general formula I above and B at least one compound containing a primary or secondary amino group or hydroxy group selected from primary or secondary aliphatic or aromatic amines, nitrogen-containing heterocyclic compounds, amino acids, oligopeptides made up of 2 to 9 amino acids and aromatic hydroxy compounds and/or at least one CH-active compound.

The above-mentioned compounds of component B may be used in a quantity of 0.03 to 65 mmol and are preferably used in a quantity of 1 to 40 mmol, based on 100 g of the colorant as a whole.

Several different isatin derivatives corresponding to formula I may even be used together in the colorants. Similarly, several different compounds of component B may also be used together. This embodiment also encompasses the use of substances which represent reaction products of isatin derivatives corresponding to formula I with the compounds B.

Suitable compounds containing a primary or secondary amino group are, for example, primary aromatic amines, such as N,N-dimethyl-, N,N-diethyl-, N-(2-hydroxyethyl)-N-ethyl-, N,N-bis-(2-hydroxyethyl)-, N-(2-methoxyethyl)-, 2,3-, 2,4-, 2,5-dichloro-p-phenylenediamine, 2-chloro-p-phenylenediamine, 2,5-dihydroxy-4-morpholinoaniline dihydrobromide, 2-, 3-, 4-aminophenol, 2-aminomethyl-4-aminophenol, 2-hydroxymethyl-4-aminophenol, o-, m-, p-phenylenediamine, o-, m-toluylenediamine, 2,5-diaminotoluene, -phenol, -phenethol, 4-amino-3-methylphenol, 2-(2,5-diaminophenyl)-ethanol, 2,4-diaminophenoxyethanol, 2-(2,5-diaminophenoxy)-ethanol, 4-methylamino-, 3-amino-4-(2'-hydroxyethyloxy)-, 3,4-methylenediamino-, 3,4-methylenedioxyaniline, 3-amino-2,4-dichloro-, 4-methylamino-, 2-methyl-5-amino-, 3-methyl-4,-amino-, 2-methyl-5-(2-hydroxyethylamino)-, 6-methyl-3-amino-2-chloro-, 2-methyl-5-amino-4-chloro-, 5-(2-hydroxyethylamino)-4-methoxy-2-methylphenol, 1,3-diamino-2,4-dimethoxybenzene, 2-, 3-, 4-aminobenzoic acid, -phenylacetic acid, 2,3-, 2,4-, 2,5-, 3,4-, 3,5-diaminobenzoic acid, 4-, 5-aminosalicylic acid, 3-amino-4-hydroxy-, 4-amino-3-hydroxybenzoic acid, 2-, 3-, 4-aminobenzenesulfonic acid, 3-amino-4-hydroxybenzenesulfonic acid, 4-amino-3-hydroxynaphthalene-1-sulfonic acid, 6-amino-7-hydroxynaphthalene-2-sulfonic acid, 7-amino-4-hydroxynaphthalene-2-sulfonic acid, 4-amino-5-hydroxynaphthalene-2,7-disulfonic acid, 3-amino-2-naphthoic acid, 3-aminophthalic acid, 5-aminoisophthalic acid, 1,3,5-, 1,2,4-triaminobenzene, 1,2,4,5-tetraaminobenzene, 2,4,5-triaminophenol, pentaaminobenzene, hexaaminobenzene, 2,4,6-triaminoresorcinol, 4,5-diaminopyrocatechol, 4,6-diaminopyrogallol, 3,5-diamino-4-hydroxypyrocatechol, aromatic anilines and phenols containing another aromatic radical corresponding to formula II:

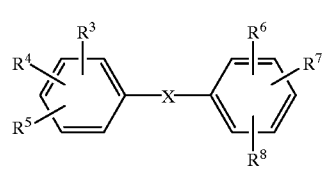

(II)

in which $R^3$ is a hydroxy group or an amino group which may be substituted by $C_{1-4}$ alkyl, $C_{1-4}$ hydroxyalkyl, $C_{1-4}$ alkoxy or $C_{1-4}$ alkoxy-$C_{1-4}$-alkyl groups, $R^4$, $R^5$, $R^6$, $R^7$ and $R^8$ represent hydrogen, a hydroxy group or an amino group which may be substituted by $C_{1-4}$ alkyl, $C_{1-4}$ hydroxyalkyl, $C_{1-4}$ alkoxy, $C_{1-4}$ aminoalkyl or $C_{1-4}$ alkoxy-$C_{1-4}$-alkyl groups or a sulfonic acid group and X is a direct bond, a saturated or unsaturated optionally hydroxy-substituted carbon chain containing 1 to 4 carbon atoms, a carbonyl, sulfonyl or amino group, an oxygen or sulfur atom or a group corresponding to formula III:

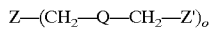

$$Z-(CH_2-Q-CH_2-Z')_o \quad (III)$$

in which

Q is a direct bond, a $CH_2$ or CHOH group,

Z and Z' independently of one another represent an oxygen atom, an $NR^9$ group, where $R^9$ is hydrogen, a $C_{1-4}$ alkyl or a hydroxy-$C_{1-4}$-alkyl group, the group O—$(CH_2)_p$—NH or NH—$(CH_2)_{p'}$—O, where p and p'=2 or 3, and o is a number of 1 to 4, such as for example 4,4'-diaminostilbene, 4,4'-diaminostilbene-2,2'-disulfonic acid monosodium or disodium salt, 4,4'-diaminodiphenyl methane, -sulfide, -sulfoxide, -amine, 4,4'-diaminodiphenylamine-2-sulfonic acid, 4,4'-diaminobenzophenone, -diphenyl ether, 3,3',4,4'-tetraaminodiphenyl, 3,3'4,4'-tetraaminobenzophenone, 1,3-bis-(2,4-diaminophenoxy)-propane, 1,8-bis-(2,5-diaminophenoxy)-3,6-dioxaoctane, 1,3-bis-(4-aminophenylamino)-propane, -2-propanol, 1,3-bis-[N-(4-aminophenyl)-2-hydroxyethylamino]-2-propanol, N,N-bis-[2-(4-aminophenoxy)-ethyl]-methylamine, N-phenyl-1,4-phenylenediamine.

The compounds mentioned above may be used both in free form and in the form of their physiologically compatible salts, more especially as salts of inorganic acids, such as hydrochloric acid or sulfuric acid.

Suitable nitrogen-containing heterocyclic compounds are, for example, 2-, 3-, 4-amino-, 2-amino-3-hydroxy-, 2,6-diamino-, 2,5-diamino-, 2,3-diamino-, 2-dimethylamino-5-amino-, 2-methylamino-3-amino-6-methoxy-, 2,3-diamino-6-methoxy-, 2,6-dimethoxy-3,5-diamino-, 2,4,5-triamino-, 2,6-dihydroxy-3,4-dimethyl pyridine, 2,4-dihydroxy-5,6-diamino-, 4,5,6-triamino-, 4-hydroxy-2,5,6-triamino-, 2-hydroxy- ,5,6-triamino-, 2,4,5,6-tetraamino-, 2-methylamino-4,5,6-triamino-, 2,4-, 4,5-diamino-, 2-amino-4-methoxy-6-methyl pyrimidine, 3,5-diaminopyrazole, -1,2,4-triazole, 3-amino-, 3-amino-5-hydroxypyrazole, 2-, 3-, 8-aminoquinoline, 4-aminoquinaldine, 2-, 6-aminonicotinic acid, 5-aminoisoquinoline, 5-, 6-aminoindazole, 5-, 7-aminobenzimidazole, -benzothiazole, 2,5-dihydroxy-4-morpholinoaniline and indole and indoline derivatives, such as 4-, 5-, 6-, 7-aminoindole, 5,6-dihydroxyindole, 5,6-dihydroxyindoline and 4-hydroxyindoline. The compounds mentioned above may be used both in free form and the form of their physiologically compatible salts, for example as salts of inorganic acids, such as hydrochloric acid or sulfuric acid.

Suitable amino acids are any naturally occurring and synthetic amino acids, for example the amino acids obtainable by hydrolysis from vegetable or animal proteins, for example collagen, keratin, casein, elastin, soya protein, wheat gluten or almond protein. Both acidic and alkaline amino acids may be used. Preferred amino acids are arginine, histidine, tyrosine, phenyl alanine, DOPA (dihydroxyphenyl alanine), ornithine, lysine and tryptophane.

The oligopeptides may be naturally occurring or synthetic oligopeptides and the oligopeptides present in polypeptide or protein hydrolyzates providing they are sufficiently soluble in water for use in the colorants according to the invention. Examples of such polypeptides are glutathione and the oligopeptides present in the hydrolyzates of collagen, keratin, casein, elastin, soya protein, wheat gluten or almond protein. These oligopeptides are preferably used together with compounds containing a primary or secondary amino group or with aromatic hydroxy compounds.

Suitable aromatic hydroxy compounds are, for example, 2-, 4-, 5-methyl resorcinol, resorcinol, 2,5-dimethyl resorcinol, 3-methoxyphenol, pyrocatechol, hydroquinone, pyrogallol, phloroglucinol, hydroxyhydroquinone, 2-, 3-, 4-methoxy-, 3-dimethylamino-, 2-(2-hydroxyethyl)-, 3,4-methylenedioxyphenol, 2,4-, 3,4-dihydroxybenzoic acid, -phenylacetic acid, gallic acid, 2,4,6-trihydroxybenzoic acid, -acetophenone, 2-, 4-chlororesorcinol, 1-naphthol, 1,5-, 2,3-, 2,7-dihydroxynaphthalene, 6-dimethylamino-4-hydroxy-2-naphthalene sulfonic acid, 3,6-dihydroxy-2,7-naphthalene sulfonic acid.

Examples of CH-active compounds are 1,2,3,3-tetramethyl-3H-indolium iodide, 1,2,3,3-tetraamethyl indolium-p-toluene sulfonate, 1,2,3,3-tetramethyl-3H-indolium methane sulfonate, 2,3-dimethylbenzothiazolium iodide, 2,3-dimethylbenzothiazolium-p-toluene sulfonate, rhodanine, rhodanine-3-acetic acid, 1-ethyl-2-quinaldinium iodide, 1-methyl-2-quinaldinium iodide, barbituric acid, thiobarbituric acid, 1,3-dimethyl thiobarbituric acid, diethyl thiobarbituric acid, oxindole, 3-indoxyl acetate, coumaranone and 1-methyl-3-phenyl-2-pyrazolinone.

In one particularly preferred embodiment, component B is selected from the group consisting of N-(2-hydroxyethyl)-N-ethyl-, 2-chloro-p-phenylenediamine, N,N-bis-(2-hydroxyethyl)-p-phenylenediamine, 4-aminophenol, p-phenylenediamine, 2-(2,5-diaminophenyl)-ethanol, 2,5-diaminotoluene, 3,4-methylenedioxyaniline, 3-amino-2,4-dichloro-, 2-methyl-5-amino-, 3-methyl-4-amino-, 2-methyl-5-(2-hydroxyethylamino)-, 2-methyl-5-amino-4-chloro-, 6-methyl-3-amino-2-chloro-, 2-aminomethyl4-aminophenol, 2-hydroxymethyl-4-aminophenol, 3,4-methylenedioxyphenol, 3,4-diaminobenzoic acid, 2,5-diamino-, 2-dimethylamino-5-amino-, 3-amino-2-methylamino-6-methoxy-, 2,3-diamino-6-methoxy-, 3,5-diamino-2,6-dimethoxy-, 2,6-dihydroxy-3,4-dimethyl pyridine, 2-hydroxy-4,5,6-triamino-, 4-hydroxy-2,5,6-triamino-, 2,4,5,6-tetraamino-, 2-methylamino-4,5,6-triaminopyrimidine, 3,5-diaminopyrazole, 3-amino-5-hydroxypyrazole, 5,6-dihydroxyindole and 5,6-dihydroxyindoline and the physiologically compatible salts thereof formed with preferably inorganic acids.

Oxidizing agents, for example $H_2O_2$, need not present. However, it may be desirable in some cases to add hydrogen peroxide or other oxidizing agents to the preparations according to the invention to obtain shades which are lighter than the keratin-containing fibers to be colored. Oxidizing agents are generally used in a quantity of 0.01 to 6% by weight, based on the solution applied. A preferred oxidizing agent for human hair is $H_2O_2$.

In another preferred embodiment, the colorants according to the invention contain typical substantive dyes, for example from the group of nitrophenylenediamines, nitroaminophenols, azo dyes, anthraquinones or indophenols, in addition to the compounds present in accordance with the invention and optionally other oxidation dye precursors in order further to modify the color tones. Preferred substantive dyes are the compounds known under the International names or commercial names of HC Yellow 2, HC Yellow 4, HC Yellow 5, HC Yellow 6, Basic Yellow 57, Disperse Orange 3, HC Red 3, HC Red BN, Basic Red 76, HC Blue 2, HC Blue 12, Disperse Blue 3, Basic Blue 99, HC Violet 1, Disperse Violet 1, Disperse Violet 4, Disperse Black 9, Basic Brown 16 and Basic Brown 17 and also 4-amino-2-nitrodiphenylamine-2'-carboxylic acid, 6-nitro-1,2,3,4-tetrahydroquinoxaline, hydroxyethyl-2- nitrotoluidine, picramic acid, 2-amino-6-chloro-4-nitrophenol, 4-ethylamino-3-nitrobenzoic acid and 2-chloro-6-ethylamino-1-hydroxy-4-nitrobenzene. The preparations according to the invention in this embodiment contain the substantive dyes in a quantity of, preferably, 0.01 to 20% by weight, based on the colorant as a whole.

In addition, the preparations according to the invention may also contain naturally occurring dyes such as, for example, henna red, henna neutral, henna black, camomile blossom, sandalwood, black tea, black alder bark, sage, logwood, madder root, catechu, sedre and alkanet.

Other dye components present in the colorants according to the invention may be indoles and indolines and physiologically compatible salts thereof. Preferred examples are 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 6-hydroxyindole, 6-aminoindole and 4-aminoindole; 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline, 6-hydroxyindoline, 6-aminoindoline and 4-aminoindoline.

The compounds of component B and optionally other oxidation dye precursors or the substantive dyes present, if any, do not have to be single compounds. Instead, the hair colorants according to the invention—due to the processes used for producing the individual dyes—may contain small quantities of other components providing they do not adversely affect the coloring result or have to be ruled out for other reasons, for example toxicological reasons.

The colorants according to the invention produce intensive colors even at physiologically compatible temperatures of <45° C. Accordingly, they are particularly suitable for coloring human hair. For application to human hair, the colorants are normally incorporated in a water-containing cosmetic carrier. Suitable water-containing cosmetic carriers are, for example, creams, emulsions, gels or even surfactant-containing foaming solutions, for example shampoos or other formulations suitable for application to the keratin-containing fibers. If necessary, the colorants may even be incorporated in water-free carriers.

The colorants according to the invention may also contain any of the known active substances, additives and auxiliaries typical of such formulations. In many cases, the colorants contain at least one surfactant, both anionic and zwitterionic, ampholytic, nonionic and cationic surfactants being suitable in principle. In many cases, however, it has been found to be of advantage to select the surfactants from anionic, zwitterionic or nonionic surfactants.

Suitable anionic surfactants for the preparations according to the invention are any anionic surface-active substances suitable for use on the human body. Such substances are characterized by a water-solubilizing anionic group such as, for example, a carboxylate, sulfate, sulfonate or phosphate group and a lipophilic alkyl group containing around 10 to 22 carbon atoms. In addition, glycol or polyglycol ether groups, ester, ether, amide groups and hydroxyl groups may also be present in the molecule.

The following are examples of suitable anionic surfactants—in the form of the sodium, potassium and ammonium salts and the mono-, di- and trialkanolammonium salts containing 2 or 3 carbon atoms in the alkanol group:

linear fatty acids containing 10 to 22 carbon atoms (soaps),
ether carboxylic acids corresponding to the formula R—O—(CH$_2$—CH$_2$O)$_x$—CH$_2$—COOH, in which R is a linear alkyl group containing 10 to 22 carbon atoms and x=0 or 1 to 16,
acyl sarcosides containing 10 to 18 carbon atoms in the acyl group,
acyl taurides containing 10 to 18 carbon atoms in the acyl group,
acyl isethionates containing 10 to 18 carbon atoms in the acyl group,
sulfosuccinic acid mono- and dialkyl esters containing 8 to 18 carbon atoms in the alkyl group and sulfosuccinic acid monoalkyl polyoxyethyl esters containing 8 to 18 carbon atoms in the alkyl group and 1 to 6 oxyethyl groups,
linear alkane sulfonates containing 12 to 18 carbon atoms,
linear α-olefin sulfonates containing 12 to 18 carbon atoms,
α-sulfofatty acid methyl esters of fatty acids containing 12 to 18 carbon atoms,
alkyl sulfates and alkyl polyglycol ether sulfates corresponding to the formula R—O(CH$_2$—CH$_2$O)$_x$—SO$_3$H, in which R is a preferably linear alkyl group containing 10 to 18 carbon atoms and x=0 or 1 to 12,
mixtures of surface-active hydroxysulfonates according to DE-A-37 25 030,
sulfated hydroxyalkyl polyethylene and/or hydroxyalkylene propylene glycol ethers according to DE-A-37 23 354,
sulfonates of unsaturated fatty acids containing 12 to 24 carbon atoms and 1 to 6 double bonds according to DE-A-39 26 344,
esters of tartaric acid and citric acid with alcohols in the form of addition products of around 2 to 15 molecules of ethylene oxide and/or propylene oxide with fatty alcohols containing 8 to 22 carbon atoms.

Preferred anionic surfactants are alkyl sulfates, alkyl polyglycol ether sulfates and ether carboxylic acids containing 10 to 18 carbon atoms in the alkyl group and up to 12 glycol ether groups in the molecule and, in particular, salts of saturated and, more particularly, unsaturated C$_{8-22}$ carboxylic acids, such as oleic acid, stearic acid, isostearic acid and palmitic acid.

In the context of the invention, zwitterionic surfactants are surface-active compounds which contain at least one quaternary ammonium group and at least one —COO$^{(-)}$ or —SO$_3^{(-)}$ group in the molecule. Particularly suitable zwitterionic surfactants are the so-called betaines, such as N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. A preferred zwitterionic surfactant is the fatty acid amide derivative known by the CTFA name of Cocamidopropyl Betaine.

Ampholytic surfactants are surface-active compounds which, in addition to a C$_{8-18}$ alkyl or acyl group, contain at least one free amino group and at least one —COOH or —SO$_3$H group in the molecule and which are capable of forming inner salts. Examples of suitable ampholytic surfactants are N-alkyl glycines, N-alkyl propionic acids, N-alkyl aminobutyric acids, N-alkyl iminodipropionic acids, N-hydroxyethyl-N-alkyl amidopropyl glycines, N-alkyl taurines, N-alkyl sarcosines, 2-alkyl aminopropionic acids and alkyl aminoacetic acids containing around 8 to 18 carbon atoms in the alkyl group. Particularly preferred ampholytic surfactants are N-cocoalkyl aminopropionate, cocoacyl aminoethyl aminopropionate and $C_{12-18}$ acyl sarcosine.

Nonionic surfactants contain, for example, a polyol group, a polyalkylene glycol ether group or a combination of polyol and polyglycol ether groups as the hydrophilic group. Examples of such compounds are products of the addition of 2 to 30 moles of ethylene oxide and/or 0 to 5 moles of propylene oxide to linear fatty alcohols containing 8 to 22 carbon atoms, to fatty acids containing 12 to 22 carbon atoms and to alkylphenols containing 8 to 15 carbon atoms in the alkyl group, $C_{12-22}$ fatty acid monoesters and diesters of products of the addition of 1 to 30 moles of ethylene oxide to glycerol, $C_{8-22}$ alkyl mono- and oligoglycosides and ethoxylated analogs thereof, products of the addition of 5 to 60 moles of ethylene oxide to castor oil and hydrogenated castor oil, products of the addition of ethylene oxide to sorbitan fatty acid esters, products of the addition of ethylene oxide to fatty acid alkanolamides.

Examples of cationic surfactants suitable for use in the hair treatment formulations according to the invention are, in particular, quaternary ammonium compounds. Preferred quaternary ammonium compounds are ammonium halides, such as alkyl trimethyl ammonium chlorides, dialkyl dimethyl ammonium chlorides and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride. Other cationic surfactants suitable for use in accordance with the invention are the quaternized protein hydrolyzates.

Also suitable for use in accordance with the invention are cationic silicone oils such as, for example, the commercially available products Q2-7224 (manufacturer: Dow Corning; a stabilized trimethyl silyl amodimethicone), Dow Corning 929 Emulsion (containing a hydroxylamino-modified silicone which is also known as Amodimethicone), SM-2059 (manufacturer: General Electric), SLM-55067 (manufacturer: Wacker) and Abil®-Quat 3270 and 3272 (manufacturer: Th. Goldschmidt; diquaternary polydimethyl siloxanes, Quaternium-80).

Alkyl amidoamines, particularly fatty acid amidoamines, such as the stearyl amidopropyl dimethyl amine obtainable as Tego Amid®S 18, are distinguished not only by their favorable conditioning effect, but also and in particular by their ready biodegradability.

Quaternary ester compounds, so-called "esterquats", such as the the dialkyl ammonium methosulfates and methyl hydroxyalkyl dialkoyloxyalkyl ammonium methosulfates marketed under the trade name of Stepantex®, are also readily biodegradable.

One example of a quaternary sugar derivative suitable for use as a cationic surfactant is the commercially available product Glucquat®100 (CTFA name: Lauryl Methyl Gluceth-10 Hydroxypropyl Dimonium Chloride).

The compounds containing alkyl groups used as surfactants may be single compounds. In general, however, these compounds are produced from native vegetable or animal raw materials so that mixtures with different alkyl chain lengths dependent upon the particular raw material are obtained.

The surfactants representing addition products of ethylene and/or propylene oxide with fatty alcohols or derivatives of these addition products may be both products with a "normal" homolog distribution and products with a narrow homolog distribution. Products with a "normal" homolog distribution are mixtures of homologs which are obtained in the reaction of fatty alcohol and alkylene oxide using alkali metals, alkali metal hydroxides or alkali metal alcoholates as catalysts. By contrast, narrow homolog distributions are obtained when, for example, hydrotalcites, alkaline earth metal salts of ether carboxylic acids, alkaline earth metal oxides, hydroxides or alcoholates are used as catalysts. The use of products with a narrow homolog distribution can be of advantage.

Other active substances, auxiliaries and additives are, for example, nonionic polymers such as, for example, vinyl pyrrolidone/vinyl acrylate copolymers, polyvinyl pyrrolidone and vinyl pyrrolidone/vinyl acetate copolymers and polysiloxanes, cationic polymers, such as quaternized cellulose ethers, polysiloxanes containing quaternary groups, dimethyl diallyl ammonium chloride polymers, acrylamide/dimethyl diallyl ammonium chloride copolymers, dimethyl aminoethyl methacrylate/vinyl pyrrolidone copolymers quaternized with diethyl sulfate, vinyl pyrrolidone/imidazolinium methochloride copolymers and quaternized polyvinyl alcohol, zwitterionic and amphoteric polymers such as, for example, acrylamidopropyl/trimethyl ammonium chloride/acrylate copolymers and octyl acrylamide/methyl methacrylate/tert.butyl aminoethyl methacrylate/2-hydroxypropyl methacrylate copolymers, anionic polymers such as, for example, polyacrylic acids, crosslinked polyacrylic acids, vinyl acetate/crotonic acid copolymers, vinyl pyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tert.butyl acrylamide terpolymers, thickeners, such as agar agar, guar gum, alginates, xanthan gum, gum arabic, karaya gum, carob bean flour, linseed gums, dextrans, cellulose derivatives, for example methyl cellulose, hydroxyalkyl cellulose and carboxymethyl cellulose, starch fractions and derivatives, such as amylose, amylopectin and dextrins, clays such as, for example, bentonite or fully synthetic hydrocolloids such as, for example, polyvinyl alcohol, structurants, such as glucose and maleic acid, hair-conditioning compounds, such as phospholipids, for example soya lecithin, egg lecithin and kephalins, and also silicone oils, protein hydrolyzates, more particularly elastin, collagen, keratin, milk protein, soya protein and wheat protein hydrolyzates, condensation products thereof with fatty acids and quaternized protein hydrolyzates, perfume oils, dimethyl isosorbide and cyclodextrins, solubilizers, such as ethanol, isopropanol, ethylene glycol, propylene glycol, glycerol and diethylene glycol, antidandruff agents, such as Piroctone Olamine and Zinc Omadine, other substances for adjusting the pH value, active substances, such as panthenol, pantothenic acid, allantoin, pyrrolidone carboxylic acids and salts thereof, plant extracts and vitamins, cholesterol, UV filters, consistency factors, such as sugar esters, polyol esters or polyol alkyl ethers, fats and waxes, such as spermaceti, beeswax, montan wax, paraffins, fatty alcohols and fatty acid esters, fatty acid alkanolamides, complexing agents, such as EDTA, NTA and phosphonic acids, swelling and penetration agents, such as glycerol, propylene glycol monoethyl ether, carbonates, hydrogen carbonates, guanidines, ureas and primary, secondary and tertiary phosphates, imidazoles, tannins, pyrrole, opacifiers, such as latex, pearlescers, such as ethylene glycol mono- and distearate, propellents, such as propane/butane mixtures, $N_2O$, dimethyl ether, $CO_2$ and air and antioxidants.

To produce the colorants according to the invention, the constituents of the water-containing carrier are used in the usual quantities for this purpose. For example, emulsifiers are used in concentrations of 0.5 to 30% by weight while thickeners are used in concentrations of 0.1 to 25% by weight, based on the colorant as a whole.

It can be of advantage to the coloring result to add ammonium or metal salts to the colorants. Suitable metal salts are, for example, formates, carbonates, halides, sulfates, butyrates, valerates, caproates, acetates, lactates, glycolates, tartrates, citrates, gluconates, propionates, phosphates and phosphonates of alkaline earth metals, such as potassium, sodium or lithium, alkaline earth metals, such as magnesium, calcium, strontium or barium, or of aluminium, manganese, iron, cobalt, copper or zinc, sodium acetate, lithium bromide, calcium bromide, calcium gluconate, zinc chloride, zinc sulfate, magnesium chloride, magnesium sulfate, ammonium carbonate, chloride and acetate being preferred. These salts are preferably present in a quantity of 0.03 to 65 mmol and more preferably in a quantity of 1 to 40 mmol, based on 100 g of the colorant as a whole.

The pH value of the ready-to-use coloring preparations is normally in the range from 2 to 11 and preferably in the range from 5 to 9.

In order to color the keratin-containing fibers, more especially human hair, the colorants are generally applied to the hair in the form of the water-containing cosmetic carrier in a quantity of 100 g, left thereon for about 30 minutes and then rinsed out or washed out with a commercially available shampoo.

The isatin derivatives corresponding to formula I and the compounds of component B may either be applied to the hair simultaneously or even successively, in which case it does not matter which of the two components is applied first. The ammonium or metal salts optionally present may be added to the first component or to the second component. A time of up to 30 minutes can be allowed to pass between application of the first component and application of the second component. The fibers may even be pretreated with the salt solution.

The isatins corresponding to formula I and the compounds of component B may be stored either separately or together either in the form of a liquid or paste-like preparation (aqueous or water-free) or as a dry powder. If the components are stored together in a liquid preparation, the preparation in question should be substantially free from water to reduce any risk of the components reacting. Where the reactive components are stored separately, they are mixed thoroughly together only shortly before application. Where the components are stored as a dry powder, a defined quantity of warm water (50 to 80° C.) is normally added and a homogeneous mixture prepared before application.

EXAMPLES

Preparation of a Coloring Solution

A suspension of 10 mmol of an isatin derivative corresponding to formula I, 10 mmol of an amino compound, 10 mmol of sodium acetate and 1 drop of a 20% fatty alkyl ether sulfate solution in 100 ml of water was prepared. The suspension was briefly heated to around 80° C. and filtered after cooling, after which the pH value was adjusted to 6.

One tress of 90% grey, non-pretreated human hair was placed in this coloring solution for 30 minutes at 30° C. The colored tress was then rinsed for 30 seconds with luke-warm water, dried in a stream of warm air (30–40° C.) and then combed. The colors were visually evaluated in daylight.

The particular shades and depths of color are shown in Table 1 below.

The depth of color was evaluated on the following scale:

| | |
|---|---|
| − | very faint, if any, color |
| (+) | weak intensity |
| + | medium intensity |
| +(+) | medium to strong intensity |
| ++ | strong intensity |
| ++(+) | strong to very strong intensity |
| +++ | very strong intensity |

TABLE 1

Coloring with 1-pyrrolidinomethyl isatin

| Component B | Shade | Depth of color |
|---|---|---|
| — | Yellow | ++ |
| 2,5-Diaminotoluene x $H_2SO_4$ | Violet red | ++(+) |
| 2,4,5,6-Tetraaminopyrimidine x $H_2SO_4$ | Red | +++ |
| 1,8-bis-(2,5-diaminophenoxy)-3,6-dioxaoctane x HCl | Red-violet | +++ |
| 2-(2,5-Diaminophenyl-ethanol x $H_2SO_4$ | Violet-red | +++ |
| 2-Aminomethyl-4-aminophenol x 2HCl | Brown-orange | ++ |
| N,N-bis-(2-hydroxyethyl)-p-phenylene-diamine x $H_2SO_4$ | Dark violet | +++ |
| 4,4'-Diaminodiphenylamine x $H_2SO_4$ | Dark olive-green | ++ |

TABLE 2

Coloring with 1-morpholinomethyl isatin

| Component B | Shade | Depth of color |
|---|---|---|
| 2,5-Diaminotoluene x $H_2SO_4$ | Violet red | ++(+) |
| 2,4,5,6-Tetraaminopyrimidine x $H_2SO_4$ | Red | ++ |
| 2-Methylamino-3-amino-6-methoxy-pyridine x 2 HCl | Yellow-orange | ++ |
| 2-(2,5-Diaminophenyl-ethanol x $H_2SO_4$ | Violet-red | ++ |
| N,N-bis-(2-hydroxyethyl)-p-phenylene-diamine x $H_2SO_4$ | Dark violet | +++ |
| 4,4'-Diaminodiphenylamine x $H_2SO_4$ | Blue-black | +++ |
| 2,6-Dimethoxy-3,5-diaminopyridine x 2HCl | Dark Grey | ++(+) |

TABLE 3

Coloring with 1-(3-carboxypropylaminomethyl)-isatin

| Component B | Shade | Depth of color |
|---|---|---|
| — | Yellow | ++ |
| 2,5-Diaminotoluene x H₂SO₄ | Violet red | ++(+) |
| 2,4,5,6-Tetraaminopyrimidine x H₂SO₄ | Copper | ++(+) |
| 2-Methylamino-3-amino-6-methoxy-pyridine x 2 HCl | Grey-violet | ++ |
| 2-(2,5-Diaminophenyl-ethanol x H₂SO₄ | Red-violet | ++(+) |
| 2-Aminomethyl-4-aminophenol x 2HCl | Brown-orange | ++(+) |
| N,N-bis-(2-hydroxyethyl)-p-phenylene-diamine x H₂SO₄ | Black-violet | +++ |
| 4,4'-Diaminodiphenylamine x H₂SO₄ | Dark violet | ++(+) |
| 2,6-Dimethoxy-3,5-diaminopyridine x 2HCl | Black | +++ |

TABLE 4

Coloring with 1-piperidinomethyl isatin

| Component B | Shade | Depth of color |
|---|---|---|
| — | Yellow | ++ |
| 2,5-Diaminotoluene x H₂SO₄ | Red-violet | ++(+) |
| 2,4,5,6-Tetraaminopyrimidine x H₂SO₄ | Violet-red | ++(+) |
| 1,8-bis-(2,5-diaminophenoxy)-3,6-dioxaoctane x 4HCl | Violet-red | ++(+) |
| 2-(2,5-Diaminophenyl-ethanol x H₂SO₄ | Violet-red | ++(+) |
| 2-Aminomethyl-4-aminophenol x 2HCl | Orange-brown | ++ |
| N,N-bis-(2-hydroxyethyl)-p-phenylene-diamine x H₂SO₄ | Dark violet | +++ |
| 4,4'-Diaminodiphenylamine x H₂SO₄ | Black | +++ |
| 2,6-Dimethoxy-3,5-diaminopyridine x 2HCl | Dark grey | ++(+) |

TABLE 5

Coloring with 1-diethylaminomethyl isatin

| Component B | Shade | Depth of color |
|---|---|---|
| — | Pure yellow | ++(+) |
| 2,5-Diaminotoluene x H₂SO₄ | Copper | ++ |
| 2,4,5,6-Tetraaminopyrimidine x H₂SO₄ | Red | ++ |
| 2-(2,5-Diaminophenyl-ethanol x H₂SO₄ | Red-brown | ++ |
| 2-Aminomethyl-4-aminophenol x 2HCl | Orange-brown | ++ |
| N,N-bis-(2-hydroxyethyl)-p-phenylene-diamine x H₂SO₄ | Dark red-violet | +++ |
| 2,6-Dimethoxy-3,5-diaminopyridine x 2HCl | Dark olive green | ++ |

TABLE 6

Coloring with 1-bis-(2-hydroxyethyl)-aminomethyl isatin

| Component B | Shade | Depth of color |
|---|---|---|
| — | Gold-yellow | ++(+) |
| 2,5-Diaminotoluene x H₂SO₄ | Red-violet | +++ |
| 2,4,5,6-Tetraaminopyrimidine x H₂SO₄ | Red | ++(+) |
| 1,8-bis-(2,5-diaminophenoxy)-3,6-dioxaoctane x 4HCl | Brown-violet | +++ |
| 2-(2,5-Diaminophenyl-ethanol x H₂SO₄ | Violet-red | ++(+) |
| 2-Aminomethyl-4-aminophenol x 2HCl | Brown-orange | ++ |
| N,N-bis-(2-hydroxyethyl)-p-phenylene-diamine x H₂SO₄ | Dark violet | +++ |
| 4,4'-Diaminodiphenylamine x H₂SO₄ | Dark violet | +++ |
| 2,6-Dimethoxy-3,5-diaminopyridine x 2HCl | Dark brown | +++ |

TABLE 7

Coloring with 1-hydroxymethyl isatin

| Component B | Shade | Depth of color |
|---|---|---|
| — | Gold-yellow | ++ |
| 2,5-Diaminotoluene x H₂SO₄ | Violet-red | ++(+) |
| 2,4,5,6-Tetraaminopyrimidine x H₂SO₄ | Rust red | ++(+) |
| 2-Methylamino-3-amino-6-methoxy-pyridine x 2 HCl | Violet | ++(+) |
| 2-(2,5-Diaminophenyl-ethanol x H₂SO₄ | Brown-violet | ++(+) |
| 2-Aminomethyl-4-aminophenol x 2HCl | Yellow-brown | ++ |
| N,N-bis-(2-hydroxyethyl)-p-phenylene-diamine x H₂SO₄ | Dark violet | +++ |
| 2,6-Dimethoxy-3,5-diaminopyridine x 2HCl | Dark brown | ++(+) |

What is claimed is:

1. A colorant composition for coloring keratin-containing fibers comprising:
   (a) at least one isatin derivative corresponding to the formula I:

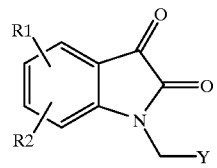

wherein $R^1$ and $R^2$ independently of one another represent a hydrogen atom, a halogen atom, a hydroxy group, a $(C_{1-4})$-alkyl, hydroxy-$(C_{1-4})$-alkyl, tertiary amino-$(C_{1-4})$-alkyl, $(C_{1-4})$-alkoxy group, an amino group optionally substituted by one or two $(C_{1-4})$-alkyl or hydroxy-$(C_{1-4})$-alkyl groups, a nitro, carboxy, or sulfo group, and Y is a hydroxy group, a $(C_{1-4})$-alkoxy group or an amino group which may be substituted by $(C_{1-4})$-alkyl, $(C_{1-4})$-alkoxy-$(C_{1-4})$-alkyl, carboxy-$(C_{1-4})$-alkyl, sulfo-$(C_{1-4})$-alkyl or hydroxy-$(C_{1-4})$-alkyl groups or which may be part of a heterocyclic 5-, 6- or 7-membered ring, or physiologically compatible salts thereof; and
   (b) at least one compound containing a primary or secondary amino group or hydroxy group selected from the group consisting of primary or secondary aliphatic or aromatic amines, nitrogen-containing heterocyclic compounds, amino acids, oligopeptides made up of 2 to 9 amino acids, aromatic hydroxy compounds, and CH-active compounds.

2. The composition of claim 1 wherein component (b) is selected from the group consisting of N-(2-hydroxyethyl)-N-ethyl-p-phenylenediamine, 2-chloro-p-phenylenediamine, N,N-bis-(2-hydroxyethyl)-p-phenylenediamine, 4-aminophenol, p-phenylenediamine, 2-(2,5-diaminophenyl)-ethanol, 2,5-diaminotoluene, 3,4-methylenedioxyaniline, 3-amino-2,4-dichloro-phenol, 2-methyl-5-amino-phenol, 3-methyl-4-amino-phenol, 2-methyl-5-(2-hydroxyethylamino)-phenol, 2-methyl-5-amino-4-chloro-phenol, 6-methyl-3-amino-2-chloro-phenol, 2-aminomethyl-4-aminophenol, 2-hydroxymethyl-4-aminophenol, 3,4-methylenedioxyphenol, 3,4-diaminobenzoic acid, 2,5-diamino-pyridine, 2-dimethylamino-5-amino-pyridine, 3-amino-2-methyl-amino-6-methoxy-pyridine, 2,3-diamino-6-methoxy-pyridine, 3,5-diamino-2,6-dimethoxy-pyridine, 2,6-dihydroxy-3,4-dimethyl pyridine, 2-hydroxy-4,5,6-triamino-pyrimidine, 4-hydroxy-2,5,6-triamino-pyrimidine, 2,4,5,6-tetraamino-pyrimidine, 2-methylamino-4,5,6-triaminopyrimidine, 3,5-diaminopyrazole, 3-amino-5-hydroxypyrazole, 5,6-dihydroxyindole and 5,6-dihydroxyindoline and physiologically compatible salts thereof.

3. The composition of claim 1 further comprising a substantive dye comprising a nitrophenylenediamine, a nitroaminophenol, an anthraquinone or an indophenol.

4. The composition of claim 1 further comprising ammonium or metal salts of formates, carbonates, halides, sulfates, butyrates, valerates, caproates, acetates, lactates, glycolates, tartrates, citrates, gluconates, propionates, phosphates or phosphonates.

5. The composition of claim 1 comprising 0.03 to 65 mmol of the isatin based on 100 g of said composition.

6. The composition of claim 5 comprising 1 to 40 mmol of the isatin based on 100 g of said composition.

7. The composition of claim 1 wherein the isatin is selected from the group consisting of 1-hydroxymethyl isatin, 1-hydroxymethyl-5-methyl isatin,1-hydroxymethyl-5-chloroisatin, 1-hydroxymethyl-5-sulfoisatin, 1-hydroxymethyl-5-carboxyisatin, 1-hydroxymethyl-5-nitroisatin, 1-hydroxymethyl-5-bromoisatin, 1-hydroxymethyl-5-methoxyisatin, 1-hydroxymethyl-5,7-dichloroisatin, 1-dimethylaminomethyl isatin, 1-diethylaminomethyl isatin, 1-(bis-(2-hydroxyethyl)-aminomethyl)isatin, 1-(2-hydroxyethylaminomethyl)-isatin, 1-(bis-(2-hydroxypropyl)-aminomethyl)-isatin, 1-pyrrolidinomethyl isatin, 1-piperidinomethyl isatin, 1-morpholinomethyl isatin, 1-(1,2,4-triazolyl)-methyl isatin, 1-(1-imidazolyl)-methyl isatin, 1-carboxymethylaminomethyl isatin, 1-(2-carboxyethylaminomethyl)-isatin, 1-(3-carboxypropylaminomethyl)-isatin, 1-(bis-(2-hydroxyethyl)-aminomethyl)-5-methyl isatin, 1-piperidinomethyl-5-chloroisatin, 1-(2-sulfoethylaminomethyl)-isatin and the alkali metal or ammonium salts thereof.

8. The composition of claim 1 wherein said composition contains no oxidizing agent.

9. The composition of claim 1 further comprising 0.01 to 6 percent by weight of an oxidizing agent.

10. The composition of claim 9 comprising $H_2O_2$ as the oxidizing agent.

11. The composition of claim 1 further comprising an anionic, zwitterionic or nonionic surfactant.

12. The composition of claim 1 further comprising a substantive dye.

13. A process for coloring keratin-containing fibers comprising:

(a) forming a colorant composition comprising at least one isatin derivative corresponding to the formula I:

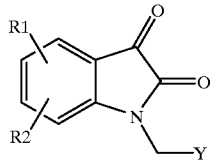

(I)

wherein $R^1$ and $R^2$ independently of one another represent a hydrogen atom, a halogen atom, a hydroxy group, a $(C_{1-4})$-alkyl, hydroxy-$(C_{1-4})$-alkyl, tertiary amino-$(C_{1-4})$-alkyl, $(C_{1-4})$-alkoxy group, an amino group optionally substituted by one or two $(C_{1-4})$-alkyl or hydroxy-$(C_{1-4})$-alkyl groups, a nitro, carboxy, or sulfo group, and Y is a hydroxy group, a $(C_{1-4})$-alkoxy group or an amino group which may be substituted by $(C_{1-4})$-alkyl, $(C_{1-4})$-alkoxy-$(C_{1-4})$-alkyl, carboxy-$(C_{1-4})$-alkyl, sulfo-$(C_{1-4})$-alkyl or hydroxy-$(C_{1-4})$-alkyl groups or which may be part of a heterocyclic 5-, 6- or 7-membered ring, or physiologically compatible salts thereof;

(b) contacting said colorant composition with keratin-containing fibers; and (c) removing said colorant composition from the keratin-containing fibers.

14. The process of claim 13 wherein said composition contacts said keratin-containing fibers for about 30 minutes.

15. The process of claim 13 wherein the isatin derivative is the sole coloring component.

16. The process of claim 13 wherein the temperature during contacting the colorant composition to the keratin containing fibers is below 45° C.

* * * * *